United States Patent
Young

(10) Patent No.: US 9,464,111 B2
(45) Date of Patent: Oct. 11, 2016

(54) SHORT PEPTIDES AND A METHOD OF USE AS AN ANTIOXIDANT

(71) Applicant: L'OREAL, Paris (FR)

(72) Inventor: Anne Young, Brooklyn, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/315,619

(22) Filed: Jun. 26, 2014

(65) Prior Publication Data
US 2015/0376234 A1 Dec. 31, 2015

(51) Int. Cl.
| | | |
|---|---|---|
| A61K 38/00 | (2006.01) | |
| C07K 5/00 | (2006.01) | |
| C07K 5/11 | (2006.01) | |
| C07K 5/117 | (2006.01) | |
| A61K 8/64 | (2006.01) | |
| A61Q 5/00 | (2006.01) | |
| A61Q 19/00 | (2006.01) | |
| A61Q 17/00 | (2006.01) | |
| C09K 15/30 | (2006.01) | |
| A23L 1/30 | (2006.01) | |
| A23L 1/305 | (2006.01) | |
| C07K 5/09 | (2006.01) | |
| C07K 5/107 | (2006.01) | |

(52) U.S. Cl.
CPC .............. *C07K 5/1019* (2013.01); *A23L 1/305* (2013.01); *A23L 1/3006* (2013.01); *A61K 8/64* (2013.01); *A61Q 5/00* (2013.01); *A61Q 17/00* (2013.01); *A61Q 19/00* (2013.01); *C07K 5/0817* (2013.01); *C07K 5/1016* (2013.01); *C07K 5/1024* (2013.01); *C09K 15/30* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 8,802,635 B2 | 8/2014 | Mograbi et al. | |
| 2005/0255176 A1* | 11/2005 | Burgess | 424/717 |
| 2011/0319347 A1 | 12/2011 | Nokihara et al. | |
| 2013/0316942 A1 | 11/2013 | Mograbi et al. | |
| 2014/0294796 A1 | 10/2014 | Wilson et al. | |
| 2014/0315787 A1 | 10/2014 | Mograbi et al. | |

FOREIGN PATENT DOCUMENTS

| | | |
|---|---|---|
| CN | 1593646 A | 3/2005 |
| JP | 2006342107 A | 12/2006 |
| JP | 2009-091305 A | 4/2009 |
| JP | 2014-015481 A | 1/2014 |
| WO | WO2004091569 A2 | 10/2004 |
| WO | WO2012119989 A2 * | 9/2012 |
| WO | WO 2013/086020 A1 | 6/2013 |

OTHER PUBLICATIONS

U.S. Appl. No. 14/315,585, filed Jun. 26, 2014, Sabatier, et al.
International Search Report and Written Opinion issued on Aug. 11, 2015 in PCT/US2015/037727.
Hang Guo, et al. "Food Chemistry", Structures and properties of antioxidative peptides derived from royal jelly protein, vol. 113, No. 1, 2009, pp. 238-245.
Gulizar Atmaca, "Antioxidant Effects of Sulfur-Containing Amino Acids" Yonsei Medical Journal, vol. 45, No. 5, (pp. 776-788), 2004.
Hailong Yang, et al., "Antioxidant Peptidomics Reveals Novel Skin Antioxidant System" Research, Skin Antioxidant Peptidomics, Molecular & Cellular Proteomics 8.3, This pa;er is available on line at http://www.mcponline.org, 2009 by The American Society for Biochemistry and Molecular Biology, Inc. (pp. 571-583) 2009.
Mingsheng Xu, et al., "Antioxidative Activity of Hen Egg Ovalbumin Hydrolysates" Original Article, Asia Pac J Clin Nutr 2007; 16 (suppl 1): (pp. 178-182).
Hau-Ming Chen, et al., "Antioxidative Properties of Histidine-Containing Peptides Designed from Peptide Fragments Found in the Digests of a Soybean Protein" Published on Web Jan. 19, 1998, American Chemical Society, J. Agric. Food Chem., vol. 46, No. 1, 1998 (pp. 49-53).
Alexander A. Boldyrev, et al., "Carnosine, the Protective, Anti-aging Peptide" Bioscience Reports, vol. 19, No. 6, 1999, (pp. 581-587).
Kesheng Zhao, et al., "Cell-Permeable Peptide Antioxidants Targeted to Inner Mitochondrial Membrane Inhibit Mitochondrial Swelling, Oxidative Cell Death, and Reperfusion Injury" Jbc, The Journal of Biological Chemistry, Affinity Sites, J. Biol. Chem. 2004, vol. 279, No. 33, (pp. 34682-34690).
Shaheen B. Mowla, et al., "A novel Stress-inducible Antioxidant Enzyme Identified from the Resurrection Plant *Xerophyta viscosa* Baker" Original Article, Planta (2002) 215: (pp. 716-726).
Barbara S. Berlett, et al., "Protein Oxidation in Aging, Disease, and Oxidative Strees" Minireview, Jbc, The Journal of Biological Chemistry, Affinity Sites, J. Biol. Chem. 1997, vol. 272, No. 33, (pp. 20313-20316).

* cited by examiner

*Primary Examiner* — James H Alstrum Acevedo
*Assistant Examiner* — Jeanette Lieb
(74) *Attorney, Agent, or Firm* — Oblon, McClelland, Maier & Neustadt, L.L.P.

(57) ABSTRACT

A short chain polypeptide having antioxidant activity is provided. The short chain polypeptide has 2 to 4 amino acids bonded to form a polypeptide chain having an amine-terminal end and a carboxyl terminal end; wherein a net charge of the short chain polypeptide is positive, the amino terminal amino acid is an amino acid selected from the group consisting of arginine, lysine and histidine, the polypeptide chain following from the amino terminus comprises a hydrophobic or neutral amino acid, and the polypeptide chain is free of an amino acid having a negatively charged side-chain group. A method to prepare a composition having antioxidant activity and a composition having antioxidant activity are also provided.

7 Claims, No Drawings

```
                           SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Arg Arg His Met
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

His Tyr His Tyr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Arg Tyr His Trp
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Arg Tyr His Met
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Trp Lys Tyr Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6
```

Trp Arg Tyr Arg
1

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Glu Glu Val Lys Arg Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Glu Glu Leu Met Ser Asp Ile Lys Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Glu Glu Met Leu Glu Arg Gln Arg Arg
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Asp Glu Ser Leu Glu Ser Thr Arg Arg Met
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Glu Glu Met Gln Arg Arg Lys Lys Lys
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

His Arg His Met
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Tyr His Phe Arg
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

His Trp Pro Tyr
1

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Tyr Trp Pro Trp
1

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

His Trp Arg Phe
1

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Cys Trp Arg Tyr Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Lys Arg Lys Tyr Trp Trp

```
<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Arg Arg Met Leu Gln Leu Val Glu Glu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Lys Lys Lys Glu Glu Met Gln Arg Arg
1               5
```

US 9,464,111 B2

SHORT PEPTIDES AND A METHOD OF USE AS AN ANTIOXIDANT

BACKGROUND OF THE INVENTION

Antioxidants are compounds which can delay or inhibit the oxidation of organic molecules by inhibition of the initiation and/or propagation of oxidizing chain reactions, generally free radical reactions. Species associated with free radical oxidation processes include peroxyl radicals (ROO.), superoxide radicals ($O_2.^-$) and hydroxyl radicals (.OH). Many natural and synthetic molecules have antioxidant properties and such character has been quantified, collected and published by the United States Department of Agriculture by listing of oxygen radical absorbance capacities (ORAC). Generally, a wide range of spices, fruits, berries and legumes have been identified as having antioxidant properties. Natural antioxidants provide platforms for the quenching of free radicals.

Conventionally employed biologically safe antioxidants include Vitamin C, Carnosine and Resveratrol. Carnosine (β-alanyl-histidine) is a natural dipeptide that is innate to vertebrates and found to act as a pH buffer, ion-chelating agent and in lipid peroxidation in vitro. Such activity for Carnosine spurs interest in peptide structures, because peptides offer a wide variety of structural modification and molecular design possibilities upon which antioxidant molecules of designed properties may be prepared.

Proteins have also been shown to have antioxidative activities against free radical oxidation of lipids and/or fatty acids. Certain peptides having electron donor properties can react with free radicals to terminate the radical chain reaction, although the exact mechanism of action for such antioxidant peptides is not clearly known. Some aromatic amino acids and histidine have been reported to play a vital role in peptides having antioxidant properties.

In view of growing demand for antioxidants designed for attractive cost and structure activity performance that may be used in food, cosmetic and other applications, economical antioxidants based on natural product raw material building blocks are sought. Proteins or long chain polypeptides having interesting antioxidant properties are known; however, the cost of producing synthetic peptides are five to twenty times higher than the cost of conventional antioxidants.

Therefore, the present inventors have studied the antioxidant properties of short polypeptide molecules and have surprisingly learned specific structure activity relationships which have led to the discovery of short chain polypeptides having antioxidant activity comparable to or better than conventionally known antioxidants such as Vitamin C, Resveratrol and Carnosine which are also cost effective.

Therefore an object of the present invention is to provide novel short chain polypeptides that have high antioxidant activity and are structurally tailored for a specific utility. The short chain polypeptides must be biologically safe and ideally at least economically competitive with the conventionally employed antioxidants described above.

A further object of the present invention is to provide a method to protect a composition from oxidation or to impart antioxidant properties to a composition.

An even further objective of the present invention is to provide a method to protect a keratinous material from free radical degradation.

SUMMARY OF THE INVENTION

These and other objects have been achieved by the present invention, the first embodiment of which includes a short chain polypeptide, comprising: 2 to 4 amino acids bonded to form a polypeptide chain having an amine-terminal end and a carboxyl terminal end; wherein a net charge of the polypeptide is positive, the amino terminal amino acid is an amino acid selected from the group consisting of arginine, lysine and histidine, the polypeptide chain following from the amino terminus comprises a hydrophobic or neutral amino acid, and the polypeptide chain is free of an amino acid having a negatively charged side-chain group.

In one embodiment of the present invention, the short chain polypeptide comprises four amino acids.

In another embodiment, the present invention includes a method to protect a composition from oxidation wherein the short chain polypeptide of the first embodiment is added to the composition.

In a further embodiment, the present invention includes a method to protect a keratinous material from free radical degradation by application of a composition containing the short chain polypeptide of the first embodiment to the keratinous material.

The foregoing paragraphs have been provided by way of general introduction, and are not intended to limit the scope of the following claims. The described embodiments, together with further advantages, will be best understood by reference to the following detailed description taken in conjunction with the appended claims.

DETAILED DESCRIPTION OF THE PREFERRED EMBODIMENTS

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. Where a numerical limit or range is stated, the endpoints are included. Also, all values and subranges within a numerical limit or range are specifically included as if explicitly written out.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

In the following description peptide sequences are described in terms of one-letter abbreviations of the amino acids according to the following chart.

| Amino acid | Abbreviation | Amino Acid | Abbreviation | Amino Acid | Abbreviation |
|---|---|---|---|---|---|
| Alanine | A | Arginine | R | Asparagine | N |
| Aspartate | D | Cysteine | C | Glutamate | E |
| Glutamine | Q | Glycine | G | Histidine | H |
| Isoleucine | I | Leucine | L | Lysine | K |
| Methionine | M | Phenylalanine | F | Proline | P |
| Serine | S | Threonine | T | Tryptophan | W |
| Tyrosine | Y | Valine | V | | |

The capital case letters represent naturally occurring amino acids in the L configuration. When a lower case letter is shown, the amino acid is in the D configuration.

According to conventional practice amino acid sequence description is provided by the one letter abbreviation sequence stated with the N-terminal end (N-terminus) amino acid first in the sequence and ending with the carboxyl terminal (carboxy terminus) amino acid. For example, the sequence RYHM (SEQ ID NO:4) is a polypeptide containing four amino acids linked via peptide bonds in the order from N-terminus to carboxy terminus: arginine-tyrosine-histidine-methionine. When the carboxyl terminus of the sequence is designated with —$NH_2$, the end carboxyl group is in the form of an amide. When the N terminal group is derivatized, the nature of the derivative is designated by standard organic chemistry abbreviations. For example, "Ac" indicates an acetyl group.

Throughout the following description, terms such as "polypeptide," "short chain polypeptide" and peptide molecule may be used interchangeably. According to the present invention, a short chain polypeptide contains 2 to 10 amino acids linked through a sequence of peptide bonds.

As understood by one of ordinary skill, the amino acids may be grouped according to the chemical structure of the side chain. Thus glycine, alanine, valine, leucine, isoleucine, methionine, tryptophan, phenylalanine and proline are described as nonpolar (hydrophobic) amino acids. Serine, threonine, cysteine, tyrosine, asparagine and glutamine are described as polar (hydrophilic), neutrally charged amino acids. Aspartic acid (aspartate) and glutamic acid (glutamate) are ionic with a negative charge and lysine, arginine and histidine are ionic with a positive charge (basic).

Standard abbreviations conventionally employed in organic chemistry may also be employed. As an example, "Ac" represents an acetyl group.

In the study of and search for molecules that have potent antioxidant activity and at the same time are biologically safe, economical to produce and may be tailored for physical properties including bioavailability, solubility and dispersibility, the inventors have recognized that polypeptides are an interesting class of molecules that have the potential to meet all the criteria for development of novel new antioxidants.

Thus a study was undertaken to understand the structural property and molecular composition parameters of polypeptide molecules that contribute to maximum antioxidant activity.

As a result of this study, the inventors have discovered the present invention, the first embodiment of which is a short chain polypeptide, comprising: 2 to 4 amino acids bonded to form a polypeptide chain having an amine-terminal end and a carboxyl terminal end; wherein a net charge of the polypeptide is positive, the amino terminal amino acid is an amino acid selected from the group consisting of arginine, lysine and histidine, the polypeptide chain following from the amino terminus comprises a hydrophobic or neutral amino acid, and the polypeptide chain is free of an amino acid having a negatively charged side-chain group.

Tables I to IX shown below are a compilation of polypeptides studied by the inventors to ascertain those elements of the molecular structure that contribute to or negate antioxidant activity. In the course of the study, polypeptides were prepared by conventional synthesis methods and screened in tubo for antioxidant activity for peroxyl radicals (ROO.), superoxide radicals ($O_2.^-$) and hydroxyl radicals (.OH).

In the screening standard testing for oxygen radical absorbance capacity (ORAC), hydroxyl radical absorbance capacity (HORAC), superoxide radical absorbance capacity (SORAC) and superoxide dismutase activity (SOD) were conducted with the test polypeptides. Testing was conducted according to USTM 190 (HORAC), USTM 191 (SORAC), USTM 192 (ORAC) and USTM 193 (SOAC) (SOD). Upon review of the results as indicated in the Tables, the inventors have discovered certain elements of the polypeptide structure as recited in claim 1 that are key contributors to determination of antioxidant activity.

Thus as shown in Table III, short chain polypeptides having neutral and/or hydrophobic amino acids at the N-terminal exhibited low or limited activity in HORAC and SORAC. Table IV shows that polypeptides having a negatively charged amino acid at the N-terminus have no activity according to both ORAC and HORAC, while Table V shows that short chain polypeptides having a positive charged (basic) amino acid at the N-terminus have high HORAC activity. In fact, the HORAC activity is 10,000 μmol GAE/g or higher and is significantly greater than the values shown in any of the previous Tables.

Table VI shows that short chain polypeptides of four or less amino acids having a net sum of positive charge across the side chain structures have the greatest overall antioxidant activity. However as indicated by Table VII, a polypeptide structure having high net positive charge, but not containing a neutral or hydrophobic amino acid had no ORAC activity. Thus as shown in Table VIII, inclusion of at least one hydrophobic and/or neutral amino acid in the amino acid sequence after the N-terminal amino acid leads to significantly higher antioxidant activity as demonstrated by the ORAC values.

Further, the inventors have discovered, that even though a given sequence may contain positively charged amino acids and neutral and/or hydrophobic amino acids, inclusion of a negatively charged (acidic) amino acid in the chain leads to a molecule having no ORAC or HORAC activity.

Thus, the inventors have discovered that the placement of the sequence and overall positive charge are crucial factors that determine the antioxidant activity of the short chain polypeptide. The first amino acid should be positively charged as a neutrally/hydrophobic and/negatively charged amino acid has limited to low antioxidant activity, especially for HORAC. Though an overall positive charge is a crucial factor contributing to antioxidant activity, a hydrophobic/neutrally charged amino acid within the chain subsequent to the N-terminal amino acid is necessary for increased activity as seen in ORAC activity. Further, the presence of negatively charged amino acids eliminates any antioxidant activity of the short chain polypeptide.

In one preferred aspect of the first embodiment, the short chain polypeptide of the present invention contains four amino acids. The inventors have taken all the information obtained from the study described above as indicated from Tables III to IX and designed the short chain polypeptides of formulas (I) to (IV) (SEQ ID NOS:1-4) as explicit embodiments of the present invention.

formula (I)

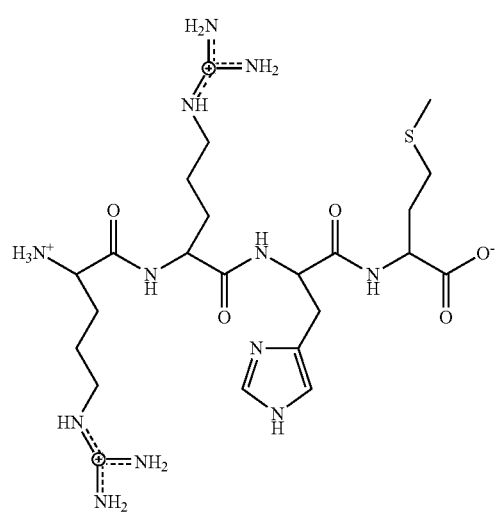

formula (II)

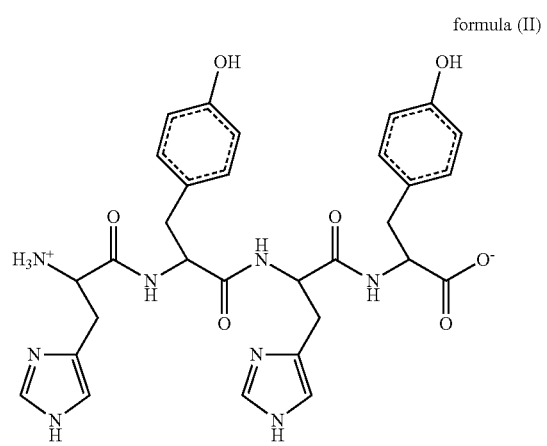

formula (III)

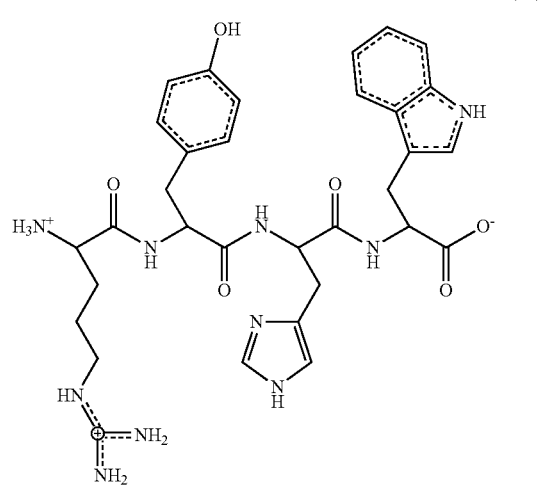

formula (IV)

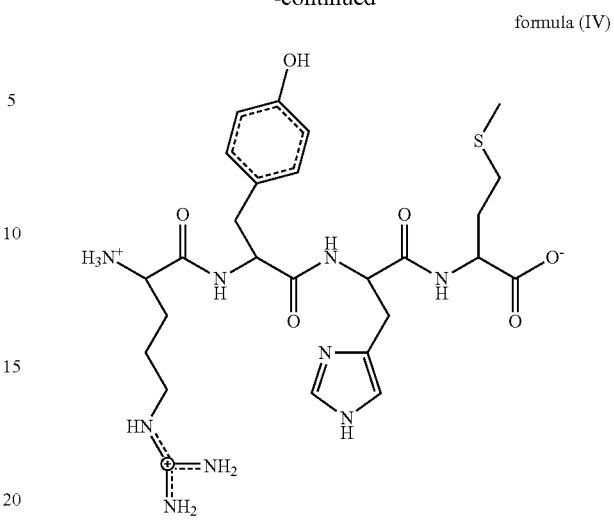

The structural formulas, mass weights, single letter abbreviation and net polypeptide charge for each of the novel short chain polypeptides are shown in Table I. ORAC, HORAC and SOD test results for each of the structures of formulas (I) to (IV) are shown in Table II. Also shown in Table II are antioxidant results for Vitamin C, Carnosine and Resveratrol. As indicated in Table II, the short chain polypeptides according to the present invention have ORAC activity comparable to those of the conventional antioxidants, while having significantly higher HORAC activity. Such increased HORAC activity is an unexpected and significant improvement obtained with the compounds of the present invention.

In another embodiment, the present invention also includes a method to prepare a composition having antioxidant properties. The method includes adding a short chain polypeptide according to the first embodiment to the composition. Thus the short chain polypeptide added comprises 2 to 4 amino acids bonded to form the polypeptide chain, wherein a net charge of the short chain polypeptide is positive, the amino terminal amino acid of the polypeptide chain is an amino acid selected from the group consisting of arginine, lysine and histidine, the polypeptide chain following from the amino terminus comprises a hydrophobic or neutral amino acid, and the polypeptide chain is free of an amino acid having a negatively charged side-chain group.

In explicit aspects of this embodiment, the short chain polypeptide may be one or more of compounds of formulas (I) to (IV).

The composition may be of any physical form including, for example, a solid, a paste, a cream, a gel or a liquid. The composition may be a solution, a dispersion, an emulsion or a suspension. The content of the short chain polypeptide according to the invention will depend upon the nature and intended use of the composition and may be easily formulated by one of ordinary skill in the respective technology of the composition.

In general the content of the short chain antioxidant polypeptide of the invention may be from 0.01 to 40 wt % of the total weight of the composition. However, the content is not limited and depending on a given utility, a content different from the range of 0.01 to 40 wt % may be employed.

In a further embodiment, the present invention includes a composition comprising a short chain polypeptide, according to the first embodiment to the composition. Thus the short chain polypeptide added comprises 2 to 4 amino acids bonded to form the polypeptide chain, wherein a net charge of the short chain polypeptide is positive, the amino terminal amino acid of the polypeptide chain is an amino acid selected from the group consisting of arginine, lysine and histidine, the polypeptide chain following from the amino terminus comprises a hydrophobic or neutral amino acid, and the polypeptide chain is free of an amino acid having a negatively charged side-chain group.

A short chain polypeptide of the invention may be advantageously formulated in a composition that may be in any galenical form normally available for the intended indication and mode of administration. The composition may comprise a physiologically or pharmaceutically acceptable medium.

According to one embodiment, a topical composition according to the invention may advantageously be formulated in any galenical form that is suitable for caring for the skin and its integuments, and may be in the form of ointments, creams, solutions, gels, emulsions, foams or aerosol compositions containing a propellant, milks, pomades, powders, impregnated pads, lotions or suspensions. A composition intended for topical administration may be an aqueous, aqueous-alcoholic or oily solution, a solution or a dispersion of the lotion or serum type, an emulsion of liquid or semiliquid consistency of the milk type, obtained by dispersing a fatty phase in an aqueous phase (O/W) or conversely (W/O), a suspension or an emulsion, of soft, semisolid or solid consistency, of the cream type or of the aqueous or anhydrous gel type, a multiple emulsion (W/O/W or O/W/O), a microemulsion, a nanoemulsion, a preparation of microcapsules, a preparation of microparticles, a vesicular dispersion of ionic and/or nonionic type, or a wax/aqueous phase dispersion.

In the case of a composition in accordance with the invention for oral administration, the use of an ingestible support, whose nature is adapted according to the type of composition under consideration, is preferred. Tablets, gel capsules or lozenges, suspensions, oral supplements in dry form and oral supplements in liquid form, milk, yoghurt, cheese, fermented milks, milk-based fermented products, ice creams, cereal-based products or fermented cereal-based products, milk-based powders, infant and baby formulae, food products of confectionery, chocolate or cereal type, and animal feed in particular for pets, are thus especially suitable as food supports.

The term "oral composition" means, for example, nutritional, nutraceutical, cosmeceutical or pharmaceutical compositions comprising at least one compound according to the invention. The formulation of the oral compositions according to the invention may be performed via any common process known to those skilled in the art for producing drinkable solutions, coated tablets, gel capsules, gels, emulsions, tablets to be swallowed or chewed, capsules, especially soft or hard capsules, granules to be dissolved, syrups, solid or liquid foods and hydrogels allowing controlled release, food bars, powders, in compacted or non-compacted form, liquid solutions or suspensions, confectioneries, fermented milk, fermented cheeses, chewing gums, toothpastes or spray solutions.

A short chain polypeptide of the invention may moreover be formulated with the usual excipients and components for such oral compositions or food supplements, i.e. especially fatty and/or aqueous components, humectants, thickeners, preserving agents, texture agents, taste agents and/or coating agents, and/or antioxidants. The formulating agents and excipients for oral compositions, and especially for food supplements, are known in this field and will not be the subject of a detailed description herein.

A composition according to the invention may also comprise any formulating agent or any cosmetically or dermatologically acceptable additional active agent. The amounts of these various active agents are those conventionally used in the field under consideration, and are especially determined so as not to affect the desired properties for a compound of the invention or for a composition of the invention.

In another embodiment, the short chain polypeptides according to the present invention may be included in nutritional compositions as an antioxidant or stabilizer of the composition that may also function as a solubilizer or as a dispersant. In other aspects of this embodiment, the short chain polypeptides according to the invention may be combined with other antioxidants to stabilize a composition to a broad spectrum of oxidative degradation mechanisms. The composition may contain nutrient fats, oils and/or proteins and may be aqueous or oil based solutions or emulsions or dry powders. In addition to the conventional antioxidants described above, other antioxidants known to one of skill in the art may be employed in combination with the short chain polypeptides of the present invention. Examples of adjuvant antioxidants may include, but are not limited to butylated hydroxy toluene, α- or β-carotene, citric acid or a derivative thereof, p-aminobenzoic acid, tocopherols and vitamins e, k and q10. One of ordinary skill may formulate an effective anti-oxidant combination for a nutritional composition employing conventional laboratory test methods.

In another embodiment, the present invention provides a method for attenuating effects of free radicals on a keratinous material by application of the composition described above to the keratinous material. The keratinous material may be human skin or hair and the composition may be in the form of, for example, a sunscreen, a skin cream, a shampoo or a hair conditioner.

The composition may be of any physical form including, for example, a solid, a paste, a cream, a gel or a liquid. The composition may be a solution, a dispersion, an emulsion or a suspension. The content of the short chain polypeptide according to the invention will depend upon the nature and intended use of the composition and may be easily formulated by one of ordinary skill in the respective technology of the composition.

In general the content of the short chain antioxidant polypeptide of the invention may be from 0.01 to 40 wt % of the total weight of the composition. However, the content is not limited and depending on a given utility, a content different from the range of 0.01 to 40 wt % may be employed.

In explicit aspects of this embodiment, the short chain polypeptide may be one or more of compounds of formulas (I) to (IV).

In another embodiment, the present invention provides a method to protect a keratinous material from free radical degradation by application of the composition described above to the keratinous material. The keratinous material may be human skin or hair and the composition may be in the form of, for example, a sunscreen, a skin cream, a shampoo or a hair conditioner.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

EXAMPLES

Method of Peptide Synthesis

N-α-Fmoc-L-amino acids, Fmoc-amide resin and reagents used for peptide synthesis were obtained from Iris Biotech. Solvents were analytical grade products from ThermoFisher. The three peptides were chemically synthesized by the solid phase method using an automated peptide synthesizer (Applied A433). Peptide chains were assembled stepwise on 0.75 meq of Fmoc-amide resin using 1 mmol of Fmoc L-amino acids.

The following reagents were used: Fmoc-amino acids (1mmol), activator (0.5 M HOBT/HBTU in dimethylformamide), base (2 M diisopropylethylamine in N-methyl-pyrrolidone) and deprotecting mixture (20% piperidine in N-methyl-pyrrolidone).

After peptide chain assembly, peptidyl-resins were treated 2 h at room temperature with a mixture of TFA/water/phenol/thioanisole/ethanedithiol (92.5/2/1/2.5/2). The peptide mixtures were then filtered, and the filtrates were precipitated by adding cold diethylether. The crude peptides were pelleted by centrifugation (3,000 g; 10 min), and the supernatants were discarded.

Peptides were purified by C18 reversed-phase (RP) High Performance/Pressure Liquid Chromatography (HPLC) using an Onyx Jupiter column (250×10 mm, 50. Elution of the peptides was performed with a linear gradient of 0 to 40% acetonitrile in 0.1% TFA (run duration of 150 min). The collected fractions were analyzed for their peptide content by analytical C18 RP-HPLC (Onyx monolithic column, 100×4.6 mm). The target peptides were characterized by matrix-assisted laser desorption ionization-time-of-flight (MALDI-TOF) mass spectrometry.

The purity of each peptide sample tested was >98%.

Peptides according to the present invention are listed in Table I. The Table shows the sequence of the peptide in one-letter abbreviation, the structural formula, the molecular weight and the net charge of the tetrapeptide.

TABLE I

| Name | Sequence | Structure | Mass (g/mol) | Net Charge |
|---|---|---|---|---|
| CP2 | RRHM (SEQ ID NO: 1) | formula (I) | 598.31 | +2.5 |
| AO1 | HYHY (SEQ ID NO: 2) | formula (II) | 618.25 | +1 |
| AO2 | RYHW (SEQ ID NO: 3) | formula (III) | 680.31 | +1.5 |
| AO2.1 | RYHM (SEQ ID NO: 4) | formula (IV) | 605.27 | +1.5 |

The peptides were tested in tubo for their antioxidant properties and tested against reference/known antioxidants. The evaluation of the antioxidant properties were conducted by determination of the ORAC (USTM 192), HORAC (USTM 190) and SOD (USTM 193) test methods. The results are listed in Table II for the peptides of the invention and for the conventionally known antioxidants

TABLE II

| Name | Sequence | ORAC/ peroxyl, μmol GAE/g | HORAC/ hydroxyl, μmol GAE/g | SOD/ superoxide, Active$_{50}$ (U/mg) |
|---|---|---|---|---|
| CP2 | RRHM (SEQ ID NO: 1) | 1204 | 321448 | |
| AO1 | HYHY (SEQ ID NO: 2) | 4748 | 33489 | 6 (Active$_{25}$) |
| AO2 | RYHW (SEQ ID NO: 3) | 9328 | 41882 | 4 (Active$_{25}$) |
| AO2.1 | RYHM (SEQ ID NO: 4) | 5390 | 132591 | |
| Supplier | | | | |
| DSM | | 4456 | 0 | 752 |
| Symrise | | 354 | 2099 | 0 |
| Symrise | | 25462 | 14190 | 626 (Active$_{25}$) |

Table III shows the results obtained for short chain polypeptides having a neutral and/or hydrophobic amino acid at the N-terminal.

TABLE III

| Name | Sequence | ORAC | HORAC | SORAC |
|---|---|---|---|---|
| RED9 | fkwR-NH2 | 2202 | 752 | No capacity |
| RED25 | WKYK-NH2 (SEQ ID NO: 5) | 4168 | 2476 | No capacity |
| RED31 | wRwR-NH2 | 4652 | — | No capacity |
| RED6 | WRYR-NH2 (SEQ ID NO: 6) | 4488 | 1548 | No capacity |
| RED18 | WrYr-NH2 | 4758 | 2982 | No capacity |
| RED19 | WRYr-NH2 | 4350 | 1457 | No capacity |
| RED20 | WrYR-NH2 | 4448 | 1666 | No capacity |
| RED21 | WRyR-NH2 | 4816 | 2472 | 7(IC25) |
| RED22 | wRyR-NH2 | 5383 | 1686 | No capacity |
| RED24 | WRYR-NH2 | 4077 | 2225 | No capacity |
| RED23 | WRYR (SEQ ID NO: 6) | 4091 | 2089 | No capacity |
| RED29 | wRyRw-NH2 | 5512 | — | No capacity |
| RED28 | wRyRy-NH2 | 5216 | — | 3(IC25) |
| RED34 | YkYkYk | 355 | 1053 | — |

Table IV shows the results obtained for short chain polypeptides having a negatively charged amino acid at the N-terminal. These sequences have no activity in both ORAC and HORAC.

TABLE IV

| Tradename | Sequence | ORAC | HORAC |
|---|---|---|---|
| AC-SYN1 | Ac-EEVKRK-NH2 (SEQ ID: 7) | No capacity | No capacity |
| AC-SYN2 | Ac-EELMSDIKK-NH2 (SEQ ID: 8) | No capacity | No capacity |
| AC-SNP3 | Ac-EEMLERQRR-NH2 (SEQ ID: 9) | No capacity | No capacity |
| AC-SNP4 | Ac-DESLESTRRM-NH2 (SEQ ID: 10) | No capacity | No capacity |
| AC-SNP5 | Ac-EEMQRRKKK-NH2 (SEQ ID: 11) | No capacity | No capacity |

Table V shows the results obtained for short chain polypeptides having a positively charged amino acid at the N-terminal.

TABLE V

| Tradename | Sequence | ORAC | HORAC | SORAC |
|---|---|---|---|---|
| CP2 | RRHM (SEQ ID NO: 1) | 1204 | 321448 | 6(IC25) |
| AO2.1 | RYHM (SEQ ID NO: 4) | 5390 | 131574 | — |
| AO2 | RYHW (SEQ ID NO: 3) | 9328 | 41882 | 4(IC25) |
| CP2.6 | RRH | 0 | 41073 | — |
| AO1 | HYHY (SEQ ID NO: 2) | 4748 | 33489 | 6(IC25) |
| CP2.5 | HRHM (SEQ ID NO: 12) | 952 | 10192 | — |

Table VI shows the results obtained for polypeptides having four or less amino acids.

TABLE VI

| Tradename | Sequence | ORAC | HORAC | SORAC | Charge (pH 7) |
|---|---|---|---|---|---|
| CP2 | RRHM (SEQ ID NO: 1) | 1204 | 321448 | 6(IC25) | 2.5+ |
| AO2.1 | RYHM (SEQ ID NO: 4) | 5390 | 131574 | | 1.5+ |
| AO2 | RYHW (SEQ ID NO: 3) | 9328 | 41882 | 4(IC25) | 1.5+ |
| CP2.6 | RRH | 0 | 41073 | | 2.5+ |
| AO1 | HYHY (SEQ ID NO: 2) | 4748 | 33489 | 6(IC25) | 1+ |
| CP2.5 | HRHM (SEQ ID NO: 12) | 952 | 10192 | | 2+ |
| IMM2 | YHFR (SEQ ID NO: 13) | | 3036 | 5(IC25) | 1+ |
| RED18 | WrYr-NH2 | 4758 | 2982 | No capacity | 2+ |
| RED25 | WKYK-NH2 (SEQ ID NO: 5) | 4168 | 2476 | No capacity | 2+ |
| RED21 | WRyR-NH2 | 4816 | 2472 | 7(IC25) | 2+ |
| RED24 | wRYR-NH2 | 4077 | 2225 | No capacity | 2+ |
| RED23 | WRYR (SEQ ID NO: 6) | 4091 | 2089 | No capacity | 2+ |
| RED22 | wRyR-NH2 | 5383 | 1686 | No capacity | 2+ |
| RED20 | WrYR-NH2 | 4448 | 1666 | No capacity | 2+ |
| RED6 | WRYR-NH2 (SEQ ID NO: 6) | 4488 | 1548 | No capacity | 2+ |
| RED19 | WRYr-NH2 | 4350 | 1457 | No capacity | 2+ |

Table VII shows the results obtained for a short chain polypeptide having a positive charge (2.5+) is important to contributing to HORAC activity, the lack of a hydrophobic/neutrally charged amino acid has given this sequence no capacity in ORAC activity.

TABLE VII

| Tradename | Sequence | ORAC | HORAC | SORAC |
|---|---|---|---|---|
| CP2.6 | RRH | No capacity | 41073 | — |

Table VIII below indicates that the presence of at least one neutral and/or hydrophobic amino acid in the chain after the N-terminal amino acid contributes to the ORAC activity.

TABLE VIII

| Tradename | Sequence | ORAC | HORAC | SORAC |
|---|---|---|---|---|
| AO2 | RYHW (SEQ ID NO: 3) | 9328 | 41882 | 4(IC25) |
| S1 | HWPY (SEQ ID NO: 14) | 5955 | — | 13(IC25) |
| S2 | YWPW (SEQ ID NO: 15) | 5917 | — | No capacity |
| RED29 | wRyRw-NH2 | 5512 | — | No capacity |

TABLE VIII-continued

| Tradename | Sequence | ORAC | HORAC | SORAC |
|---|---|---|---|---|
| AO2.1 | RYHM (SEQ ID NO: 4) | 5390 | 131574 | |
| RED22 | wRyR-NH2 | 5383 | 1686 | No capacity |
| RED27 | Ac-wRyR-NH2 | 5342 | — | No capacity |
| RED28 | wRyRy-NH2 | 5216 | — | 3(IC25) |
| RED21 | WRyR-NH2 | 4816 | 2472 | 7(IC25) |
| RED18 | WrYr-NH2 | 4758 | 2982 | No capacity |
| AO1 | HYHY (SEQ ID NO: 2) | 4748 | 33489 | 6(IC25) |
| RED31 | wRwR-NH2 | 4652 | — | No capacity |
| RED6 | WRYR-NH2 (SEQ ID NO: 6) | 4488 | 1548 | No capacity |
| RED26 | RwRyR-NH2 | 4461 | — | No capacity |
| RED20 | WrYR-NH2 | 4448 | 1666 | No capacity |
| RED19 | WRYr-NH2 | 4350 | 1457 | No capacity |
| RED25 | WKYK-NH2 (SEQ ID NO: 5) | 4168 | 2476 | No capacity |
| RED23 | WRYR (SEQ ID NO: 6) | 4091 | 2089 | No capacity |
| RED24 | wRYR-NH2 | 4077 | 2225 | No capacity |
| RED32 | RyR-NH2 | 3385 | — | No capacity |
| IMM1 | HWRF (SEQ ID NO: 16) | 2422 | — | 5(IC25) |
| RED9 | fkwR-NH2 | 2202 | 752 | No capacity |
| RED7 | kfRw-NH2 | 2120 | 1124 | No capacity |
| RED11 | CWRYR-NH2 (SEQ ID NO: 17) | 2007 | 625 | No capacity |
| RED2 | KRKYWW-NH2 (SEQ ID NO: 18) | 1837 | 1063 | No capacity |

Table IX shows results obtained for polypeptides containing a negatively charged amino acid. These sequences have no activity in both ORAC and HORAC. It shows that despite the presence of positively charge amino acids and neutral/hydrophobic amino acids, these peptide sequences have no antioxidant activity.

TABLE IX

| Tradename | Sequence | ORAC | HORAC |
|---|---|---|---|
| AC-SYN1 | Ac-EEVKRK-NH2 (SEQ ID: 7) | No capacity | No capacity |
| AC-SYN2 | Ac-EELMSDIKK-NH2 (SEQ ID: 8) | No capacity | No capacity |
| AC-SNP1 | Ac-RRMLQLVEE-NH2 (SEQ ID: 19) | No capacity | No capacity |
| AC-SNP3 | Ac-EEMLERQRR-NH2 (SEQ ID: 9) | No capacity | No capacity |
| AC-SNP4 | Ac-DESLESTRRM-NH2 (SEQ ID: 10) | No capacity | No capacity |
| AC-SNP5 | Ac-EEMQRRKKK-NH2 (SEQ ID: 11) | No capacity | No capacity |
| AC-SNP6 | Ac-Valérate-EEMQRRKKK-NH2 (SEQ ID: 11) | No capacity | No capacity |
| AC-SNP7 | Ac-KKKEEMQRR-NH2 (SEQ ID: 20) | No capacity | No capacity |

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A short chain polypeptide, comprising:

4 amino acids bonded to form a polypeptide chain having an amine-terminal end and carboxyl terminal end;

wherein the carboxy-terminal end is amidated;

wherein the net charge of the polypeptide is positive, the amino terminal amino acid is an amino acid selected from the group consisting of arginine, lysine and histidine, and the polypeptide chain following from the amino terminus comprises a hydrophobic or neutral amino acid, and the polypeptide chain is free of an amino acid having a negatively charged side-chain group;

and wherein the polypeptide is selected from the group consisting of formula (I), formula (II) and formula (III):

(SEQ ID NO: 1)

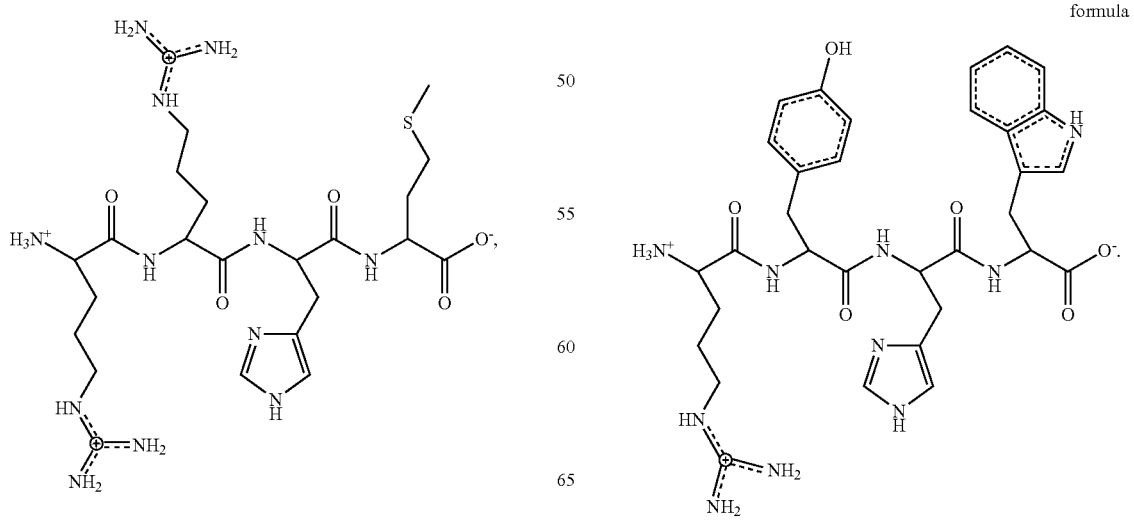

formula (I)

(SEQ ID NO: 2)

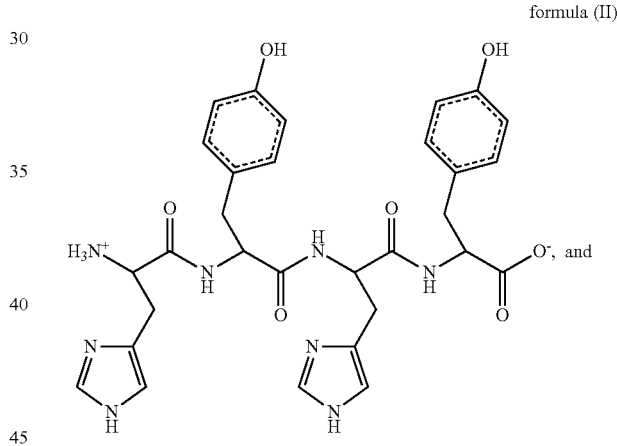

formula (II), and (SEQ ID NO: 3)

formula (III)

2. A method to prepare a composition having antioxidant properties, comprising:
adding the short chain polypeptide of claim 1 to the composition.

3. A composition, comprising:
the short chain polypeptide of claim 1 in a physiologically or pharmaceutically acceptable medium.

4. The composition of claim 3, further comprising an antioxidant that is not a short chain polypeptide.

5. The composition of claim 3, further comprising a nutritional ingredient selected from the group consisting of a fat, an oil and a protein.

6. The composition of claim 3, wherein a content of the short chain polypeptide is from 0.01 to 40 wt % based on a total weight of the composition.

7. A method for attenuating effects of free radicals on a keratinous material, comprising applying the composition of claim 3, to the keratinous material of a subject in need thereof.

* * * * *